(12) United States Patent
Yang et al.

(10) Patent No.: US 10,598,633 B2
(45) Date of Patent: Mar. 24, 2020

(54) ULTRASONIC SENSING DEVICE

(71) Applicant: National Taipei University of Technology, Taipei (TW)

(72) Inventors: Che-Hua Yang, Taipei (TW); Yi-Lin Wu, Taipei (TW); Chin-Chi Cheng, Taipei (TW)

(73) Assignee: NATIONAL TAIPEI UNIVERSITY OF TECHNOLOGY, Taipei (TW)

( * ) Notice: Subject to any disclaimer, the term of this patent is extended or adjusted under 35 U.S.C. 154(b) by 235 days.

(21) Appl. No.: 15/918,290

(22) Filed: Mar. 12, 2018

(65) Prior Publication Data

US 2019/0277810 A1    Sep. 12, 2019

(51) Int. Cl.
*G01N 29/24* (2006.01)
*B29C 45/76* (2006.01)

(52) U.S. Cl.
CPC ......... *G01N 29/2437* (2013.01); *B29C 45/76* (2013.01); *B29C 2945/7621* (2013.01); *B29C 2945/76474* (2013.01); *G01N 2291/022* (2013.01)

(58) Field of Classification Search
CPC .. B29C 2945/7621; B29C 2945/76474; B29C 45/76; G01N 2291/022; G01N 2291/0251; G01N 29/043; G01N 29/223; G01N 29/227; G01N 29/228; G01N 29/2437
See application file for complete search history.

(56) References Cited

U.S. PATENT DOCUMENTS

2016/0022928 A1* 1/2016 Cheng .................. A61M 11/005

* cited by examiner

*Primary Examiner* — Nimeshkumar D Patel
*Assistant Examiner* — Gedeon M Kidanu
(74) *Attorney, Agent, or Firm* — Muncy, Geissler, Olds & Lowe, P.C.

(57) ABSTRACT

An ultrasonic sensing device includes a support body and an ultrasonic sensor. The support body includes an accommodating space, and a positioning space at a center of the accommodating space. The ultrasonic sensor includes a body portion in the positioning space, at least one sensing channel portion extending from the body portion and in the accommodating space, at least one piezoelectric unit at one end surface of the sensing channel portion, and a second channel passing through the body portion. An inner diameter of the positioning space is greater than an inner diameter of the accommodating space, and an outer diameter of the sensing channel portion is smaller than the inner diameter of the accommodating space. Thus, a gap is formed between the sensing channel portion and the accommodating space, and the piezoelectric unit is located outside the accommodating space to come into contact with an exterior.

9 Claims, 6 Drawing Sheets

ULTRASONIC SENSING DEVICE

FIELD OF THE INVENTION

The present invention relates to an ultrasonic sensing device, and particularly to an ultrasonic sensing device having a high strength installation structure and low noise.

BACKGROUND OF THE INVENTION

To measure conditions of a high-temperature and high-pressure molten liquid in an injection molding device, non-contact measurement is usually conducted by using an ultrasonic sensor. To protect the ultrasonic sensor, an additional fixing element is usually used to mount the ultrasonic sensor at an outer periphery of the injection molding device to further perform the measurement.

However, when performing measurement by the above means, separation caused by numerous interfaces exist between the ultrasonic sensor and the molten liquid. That is to say, ultrasonic signals transmitted from the ultrasonic sensor need to pass through numerous interfaces such as the additional fixing element and the injection molding device before they can arrive at the molten liquid, and then become reflected by the molten liquid, resulting in indirect effects upon the detection mechanism. In other words, the ultrasonic signals, after passing through many indirect interfaces, form a non-direct wave interface, which not only reduces the signal strength and generates signal interference but also easily and directly affects an outcome of signal parsing. As a result, additional signal processing may be needed, causing tedious and time-consuming technical actions.

SUMMARY OF THE INVENTION

In view of the above, it is a primary object of the present invention to provide an ultrasonic sensing device, and more particularly an ultrasonic sensing device having a high strength installation structure and low noise.

According to the above object, the present invention provides an ultrasonic sensing device including a support body and an ultrasonic sensor. The support body includes two cover portions. Each of the two cover portions includes a first surface, a second surface opposite to the first surface, a recess formed at the first surface, and a first channel passing from the recess through the second surface. A composite surface is formed at a center of each of the recesses, and the first surfaces of the two cover portions are correspondingly disposed, such that the two recesses mutually correspond and jointly define an accommodating space have two opposite openings. A positioning space is jointly defined by the two composite surfaces at a center of the accommodating space, and an inner diameter of the positioning space is greater than an inner diameter of the accommodating space. The ultrasonic sensor is placed in the accommodating space, and includes a body portion provided in the positioning space, at least one sensing channel portion provided at the body portion and extending towards opposite directions so as to be located in the accommodating space, at least one piezoelectric unit located at an end surface of the sensing channel portion, and a second channel passing through the body portion. An outer diameter of the sensing channel portion is slightly smaller than the inner diameter of the accommodating space, such that a gap is formed between the sensing channel portion and the accommodating space. The piezoelectric unit is exposed from one of the openings of the accommodating space so as to come into contact with an exterior. The two first channels and the second channel are located on one axial line.

In one embodiment, the ultrasonic sensor includes two of the sensing channel portions located at the body portion and respectively extending towards opposite directions, and two of the piezoelectric units respectively located at one end surfaces of the two sensing channel portions. The piezoelectric units are respectively exposed from the two openings of the accommodating space so as to come into contact with an exterior.

In one embodiment, each of the recesses is defined by a recessed plane formed downwards from the first surface, and each of the composite surfaces is formed by two of an inclined plane, a polygon and a curved plane. The first channel is formed at the composite surface.

In one embodiment, a height difference exists at each of the two ends of the composite surface, such that a step structure is formed at a junction of the positioning space and the accommodating space.

In one embodiment, a cross section of the second channel includes two arc regions arranged at an interval and a flat plane region located between the two arc regions. The two flat plane regions are parallel to the two end surfaces of the body portion.

In one embodiment, the support body further includes an extension portion extending from the second surface of one of the cover portions towards away from the cover portion, and one of the first channel extends into the extension portion.

In one embodiment, the support body further includes a fixing portion provided at one end of the extension portion opposite to the extension portion.

In one embodiment, the support body further includes a noise resistant layer covering outer surfaces of the cover portions.

In one embodiment, each of the two cover portions further includes a plurality of screw holes formed outside the two recesses and matching one another, and the ultrasonic sensing device further includes a fastening unit that fixes the two cover portions through the screw holes.

With the above technical solution, the present invention provides substantial and effective results compared to the prior art.

In the present invention, the ultrasonic sensor is securely clamped in the positioning space between the two cover portions, the gap is formed between the sensing channel portion and the accommodating space, and the piezoelectric unit is exposed from any of the openings or from the two openings of the accommodating space when the two ends of the ultrasonic sensor are simultaneously provided with the piezoelectric unit. Thus, when an object under detection passes the two first channels and the second channel located on the same axial line, the piezoelectric unit directly performs measurement, and a structure reducing signal noise is constructed through the gap.

DETAILED DESCRIPTION OF THE PREFERRED EMBODIMENTS

Figure 1:
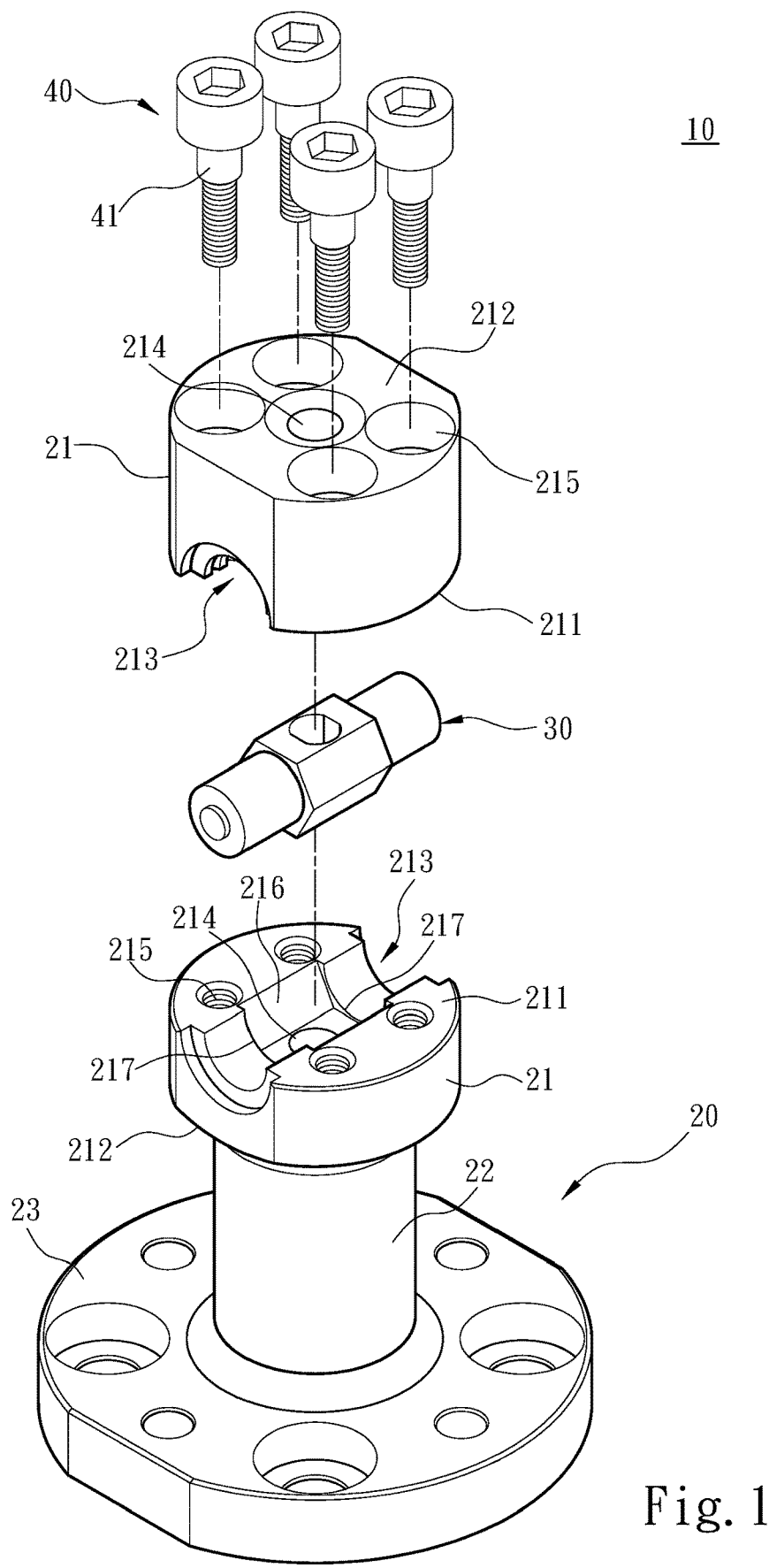
FIG. 1 is an exploded schematic diagram of a first embodiment of the present invention.
Figure 2:
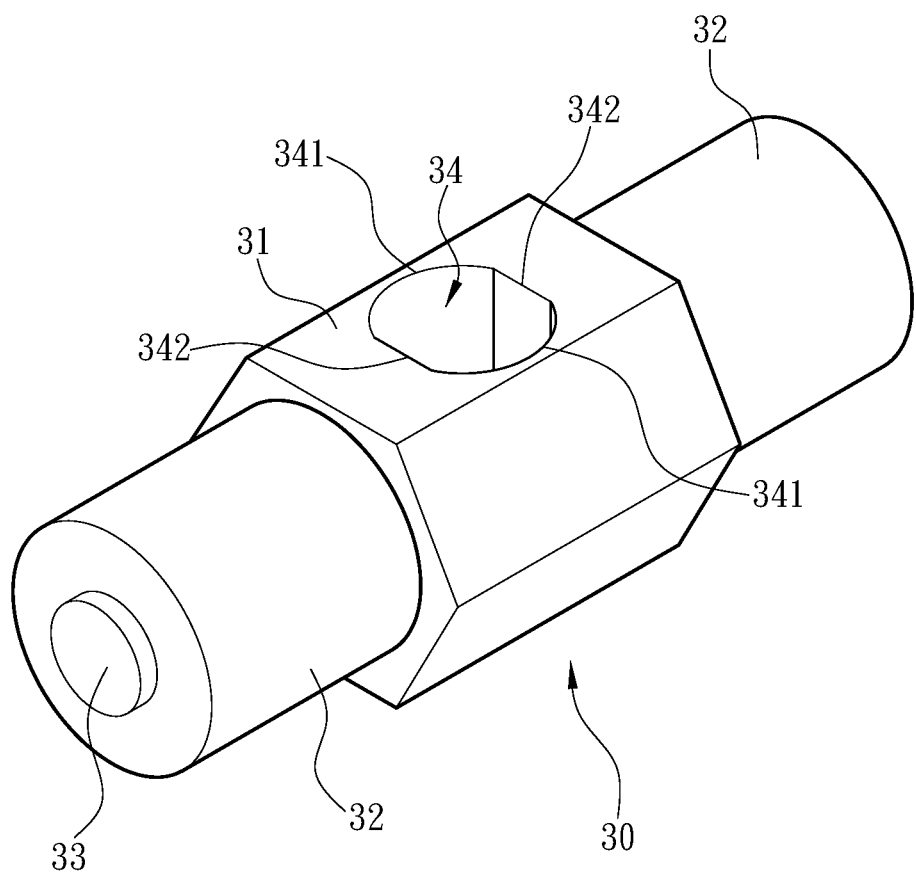
FIG. 2 is a perspective schematic diagram of an ultrasonic sensor according to the first embodiment of the present invention.
Figure 3:
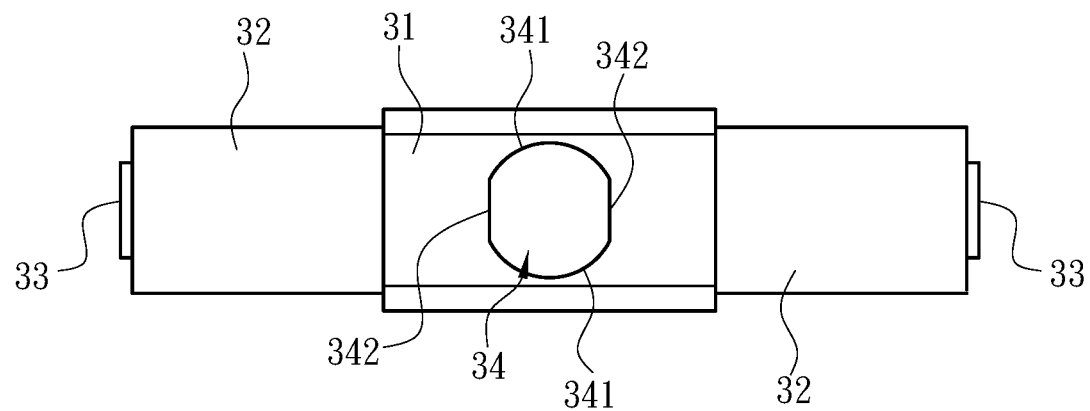
FIG. 3 is a top view of an ultrasonic sensor according to the first embodiment of the present invention.

Details and technical contents of the present invention are described with the accompanying drawings below.

Referring to FIG. 1, FIG. 2, FIG. 3 and FIG. 4, as shown in the drawings, the present invention provides an ultrasonic sensing device 10 including a support body 20, an ultrasonic sensor 30 provided in the support body 20, and a fastening unit 40. The support body 20 includes two cover portions 21, an extension portion 22 extending from one of the cover portions 21, and a fixing portion 23 provided at one end of the extension portion 22 opposite to the cover portion 21. More specifically, each of the cover portions 21 includes a first surface 211, a second surface 212 opposite to the first surface 211, a recess 213 formed at the first surface 211, a first channel 214 passing from the recess 213 through the second surface 212, and a plurality of screw holes 215 formed at the first surface 211 and located outside the recesses 213. More specifically, the recess 213 of each of the cover portions 21 is defined by an arc curved concave surface formed downwards from the first surface 211, and a composite surface 216 is formed at a center of the recess 213 by an inclined plane, a polygon or a curved plane. The first channel 214 is formed at the composite surface 216 and passes through to the second surface 212. Each of the two ends of the composite surface 216 comprises a height difference and thus forms a step structure 217. The extension portion 22 extends from the second surface 212 of one of the cover portions 21 towards away from the cover portion 21, and one of the first channels 214 extends into the extension portion 22. The fixing portion 23 extends outwards from one end of the extension portion 22 opposite to the cover portion 21 to substantially appear as a disc-shape, and includes a plurality of holes for connecting to an external device.

In this embodiment, the first surfaces 211 of the two cover portions 21 are arranged facing each other, and the recesses 213 of the two cover portions 21 are mutually correspondingly disposed, such that the two recesses 213 on the two cover portions 21 jointly define an accommodating space 201, and the two composite surfaces 216 on the two cover portions 21 jointly define a positioning space 202. The positioning space 202 is located at a center of the accommodating space 201 to separate the accommodating space 201 into two parts, providing the accommodating space 201 with two opposite openings 203 substantially appearing as cylindrical spaces. Thus, the ultrasonic sensor 30 can be placed in the positioning space 202 and the accommodating space 201. Further, with the matching of the plurality of screw holes 215 of the two cover portions 21, a plurality of fastening members 41 of the fastening unit 40 are penetrated into the plurality of screw holes 215 to connect the two cover portions 21, thus securely locating the ultrasonic sensor 30 in the positioning space 202 and the accommodating space 201. It should be noted that, the plurality of fastening members 41 are exemplified by four screws, and are not limited thereto, as long as the two cover portions 21 can be fixed and the ultrasonic sensor 30 can be securely located in the positioning space 202 and the accommodating space 201.

The ultrasonic sensor 30 is extendedly provided in the accommodating space 201 and the positioning space 202, and includes a body portion 31 having a size and a shape both substantially matching those of the positioning space 202, two sensing channel portions 32 provided at the body portion 31 and extending towards opposite directions so as to be located in the accommodating space 201, two piezoelectric units 33 respectively provided at one of the end surfaces of the two sensing channel portions 32, and a second channel 34 passing through the body portion 31. The body portion 31 of the ultrasonic sensor 30 is provided in the positioning space 202 defined by the two composite surfaces 216, and the two sensing channel portions 32 are provided in the accommodating space 201 defined by the two recesses 213. An outer diameter of each of the two sensing channel portions 32 is slightly smaller than the inner diameter of the accommodating space 201. The second channel 34 and the two first channels 214 are located on the same axial line and are connected to each other, and the two piezoelectric units 33 are respectively exposed from the two openings 203 of the accommodating space 201 so as to contact with an exterior.

It should be noted that, in this embodiment, each of the two junctions of the accommodating space 201 and the positioning space 202 divided by the recess 213 and the composite surface 216 comprises the step structure 217. In other words, the inner diameter of the positioning space 202 is greater than the inner diameter of the accommodating space 201. Thus, an outer periphery of the body portion 31 of the ultrasonic sensor 30 is designed to match the two composite surfaces 216. That is to say, the part of the body portion 31 of the ultrasonic sensor 30 from the outer diameter of the sensing channel portion 32 corresponding to the positioning space 202 evenly protrudes towards a radial direction, such that the body portion 31 is tightly engaged in the positioning space 202. The two sensing channel portions 32 on the two side of the body portion 31 are respectively located in the two accommodating spaces 201. The inner diameter of the accommodating space 201 is slightly greater than the inner diameter of the sensing channel portion 32, such that a gap 50 is formed between an outer wall of the two sensing channel portions 32 and an interior of the accommodating space 201.

To install the ultrasonic sensing device 10 of the present invention to an injection molding device (not shown), the ultrasonic sensing device 10 is installed on an injection nozzle of the injection molding device primarily by penetrating a plurality of screws through the plurality of holes of the fixing portion 23. The design of the fixing portion 23 may differ according to different injection molding devices to enable the ultrasonic sensing device 10 to be simply and quickly installed or removed. More specifically, when the ultrasonic sensing device 10 is installed on the injection nozzle, a molten liquid in the injection molding device flows from the first channel 214 to the second channel 34, and can be detected by applying and receiving ultrasonic signals through the piezoelectric unit 33 located at the exterior of the two sensing channel portions 32.

It should be noted that, the two cover portions 21 of the ultrasonic sensing device 10 of the present invention are in a top-bottom engagement to cause the ultrasonic sensor 30 to be fastened therein, and the piezoelectric units 33 are caused to be located on the two sides of the molten liquid flowing through. Thus, the ultrasonic sensor 30 is enabled to resist against the high voltage that the molten liquid generates in the second channel 34. Further, because the body portion 31 of the ultrasonic sensor 30 is enveloped in the positioning space 202 formed by the inclined plane, the polygon or the curved plane, the pressure received at two corresponding sides of the body portion 31 is even when the molten liquid flows through the second channel 34 of the ultrasonic sensor 30, allowing the second channel 34 to form a stable operating structure interval.

To reduce the interference and noise during the detection process performed by the ultrasonic sensor 30 on the molten liquid, a noise resistant layer (not shown) covering outer surfaces of the two cover portions 21 may further be formed. The noise resistant layer primarily uses a high strength noise reduction material, which is applied at a high temperature and sintered on the outer surface of the cover portion 21, providing the ultrasonic sensor 30 with noise reduction performance. Further, when the body portion 31 of the ultrasonic sensor 30 is clamped in the positioning space 202, through the gap 50 between the accommodating space 201 and the two sensing channel portions 32, a contact area between the ultrasonic sensor 30 and the two cover portions 21 is reduced, further providing a structure with good noise reduction performance.

It should be noted that, a cross section of the second channel 34 of the ultrasonic sensor 30 is not a current circular cross section, but is formed by two facing arc regions 341 at an interval and a flat plane region 342 between the two arc regions 341. The two flat plane regions 342 are substantially parallel to the end surfaces of the body portion 31. When the molten liquid flows to the second channel 34, the combined configuration of the arc regions 341 and the flat plane region 342 generates a temporary stop-over effect on the viscoelastic molten liquid flowing in laminar flow, thus providing the two piezoelectric units 33 with reliable and stable detection.

Figure 5:
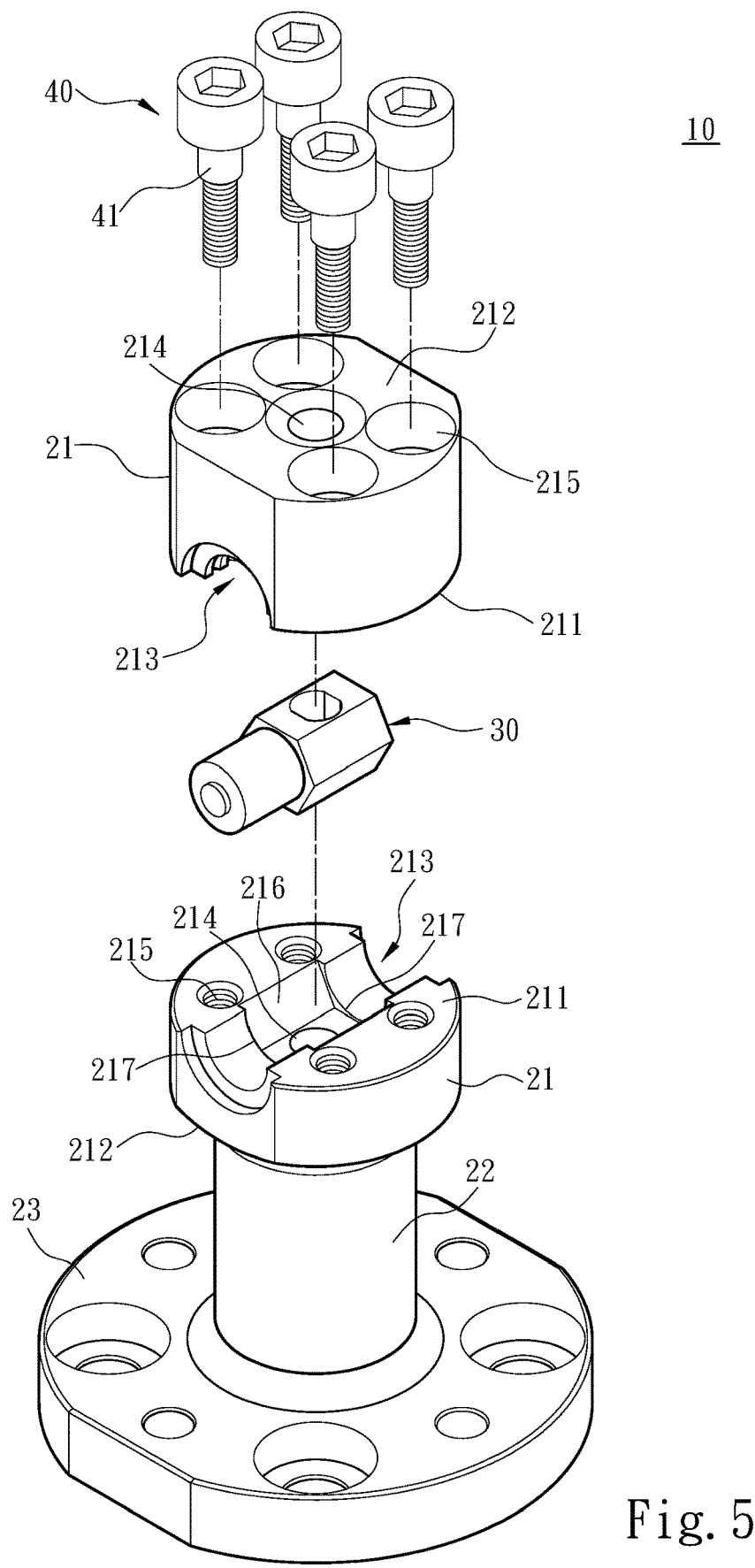
FIG. 5 is an exploded schematic diagram of a second embodiment of the present invention.
Figure 6:
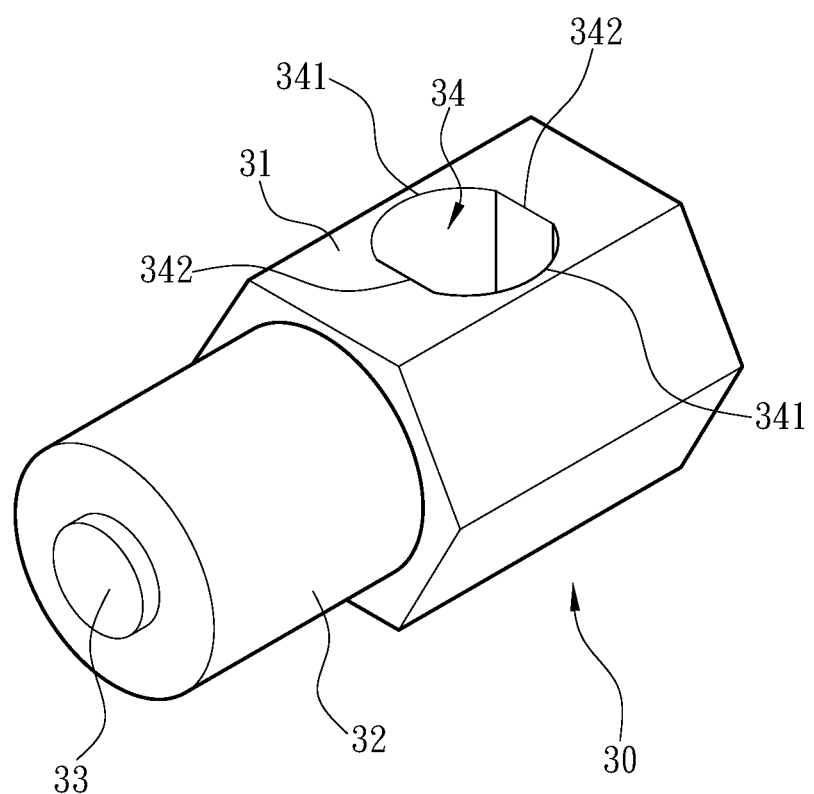
FIG. 6 is a perspective schematic diagram of an ultrasonic sensor according to the second embodiment of the present invention.

Further, as shown in FIG. 5 and FIG. 6, in this embodiment, the ultrasonic sensor 30 is provided with a sensing channel portion 32 by extending from one side of the body portion 31, and a piezoelectric unit 33 is provided on an outer side of the sensing channel portion 32. In other words, the piezoelectric unit 33 may be provided at only one of the end surfaces of the body portion 31. At this point, the piezoelectric unit 33 may be caused to transmit and receive ultrasonic signals by a pulse-echo mechanism. Alternatively, as the embodiment shown in FIG. 2, the piezoelectric unit 33 may be provided at each of two opposite end surfaces of the body portion 31, and one of the piezoelectric unit 33 is caused to transmit ultrasonic signals whereas the other piezoelectric unit 33 is caused to receive ultrasonic signals by a pulse-transmit mechanism, thus realizing arrangements and detection applications of different detection groups.

Figure 4:
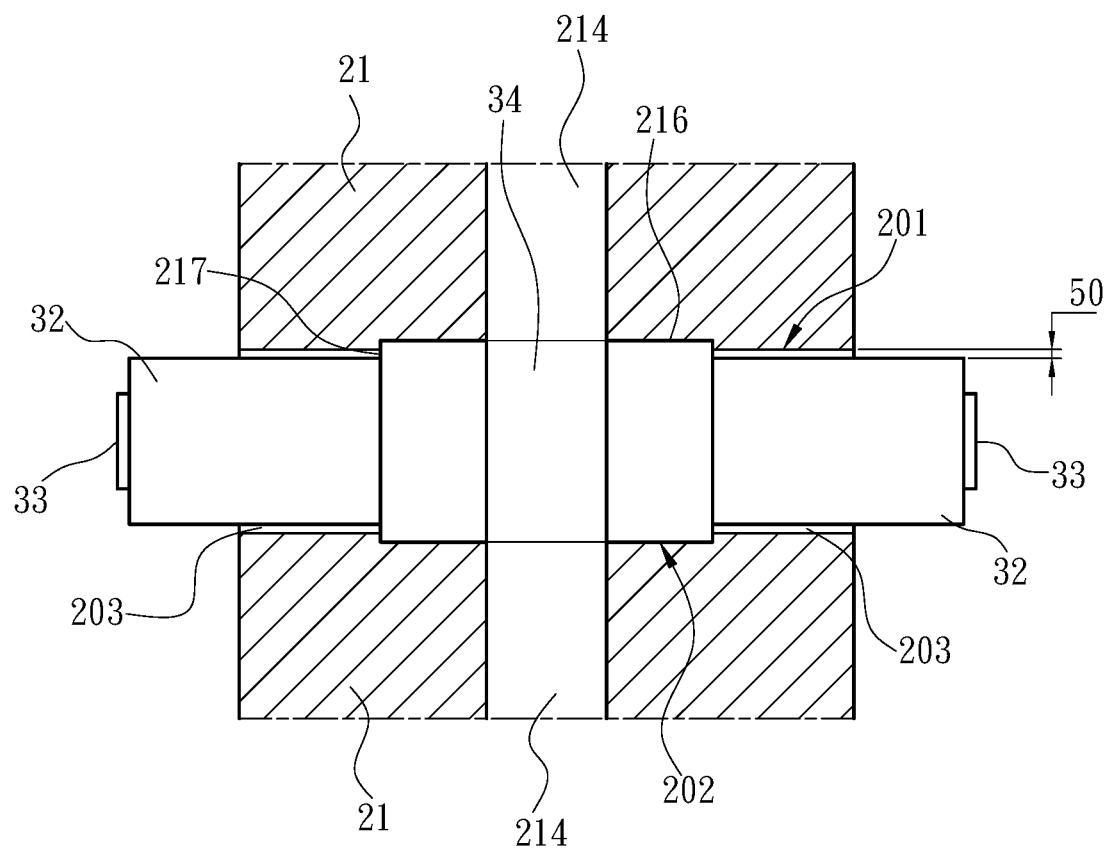
FIG. 4 is a sectional schematic diagram of the first embodiment of the present invention.
Figure 7:
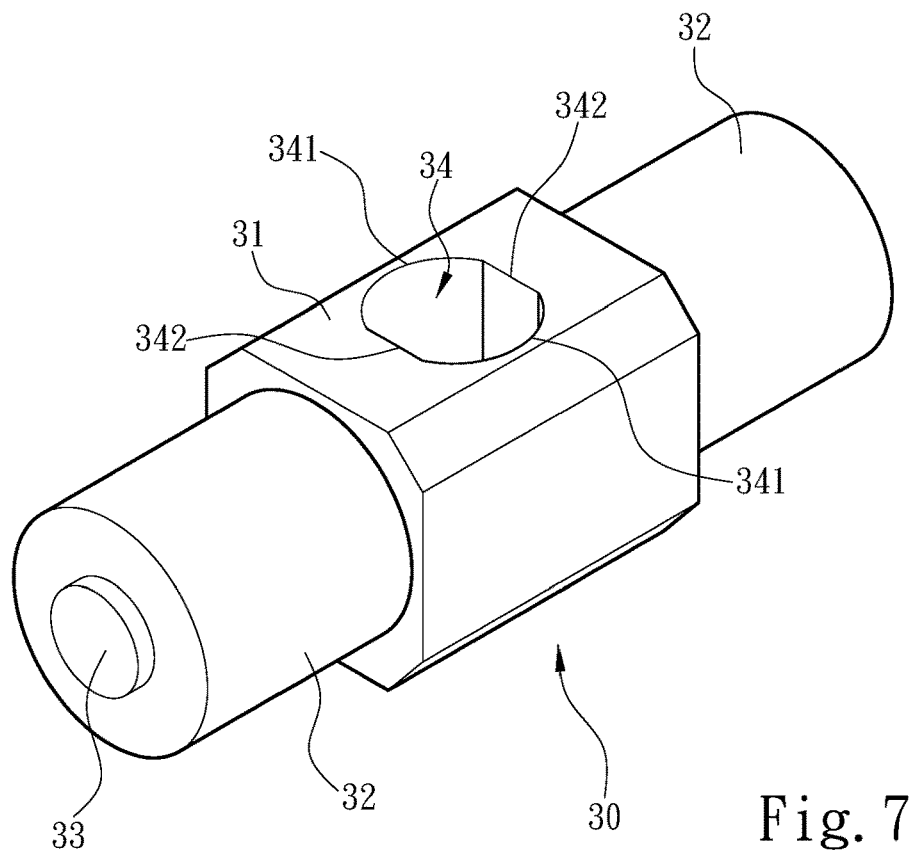
FIG. 7 is a perspective schematic diagram of an ultrasonic sensor according to a third embodiment of the present invention.
Figure 8:
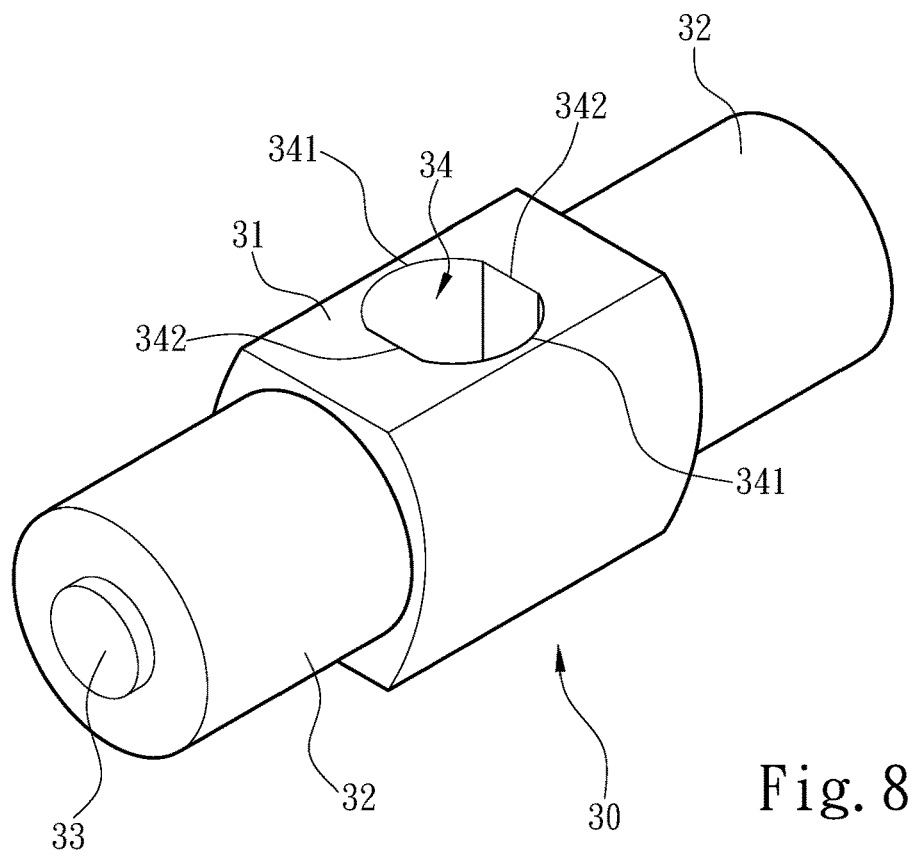
FIG. 8 is a perspective schematic diagram of an ultrasonic sensor according to a fourth embodiment of the present invention.

As shown in FIG. 7 and FIG. 8, the body portion 31 of the ultrasonic sensor 30 has the same size and the same shape as the positioning space 202 (as shown in FIG. 4), and the positioning space 202 is formed by the composite surface 216 defined by two of an inclined plane, a polygon and a curved plane. Thus, the body portion 31 can be effectively secured in the positioning space 202, and the body portion 31 is effectively prevented from rotating in the positioning space 202, further preventing dislocation occurring between the first channel 214 and the second channel 34.

In conclusion, in the ultrasonic sensing device 10 of the present invention, the two recesses 213 and the two composite surfaces 216 of the cover portions 21 are correspondingly provided, and a matching step structure 217 is further designed, thus securely arranging the ultrasonic sensor 30 in the positioning space 202. Further, the sensing channel portion 32 is caused to form the gap 50 in the accommodating space 201, and a contact mechanism of the noise resistant layer covering the outer surfaces of the two cover portions 21 and the two recesses 213 is provided, further reducing reflection waves between the body portion 31 and the two cover portions 21 to provide good noise reduction performance. Further, the cross section of the second channel 34 of the ultrasonic sensor 30 is designed as a combination of the arc regions 341 and the flat plane region 342, providing more reliable and stable detection and achieving the objects of the present invention.

What is claimed is:

1. An ultrasonic sensing device, comprising:
a support body, comprising two cover portions, each of the cover portions comprising a first surface, a second surface opposite to the first surface, a recess formed at the first surface, and a first channel passing from the recess through the second surface, a composite surface formed at a center of each of the recesses, the first surfaces of the two cover portions mutually arranged to allow the two recesses to mutually correspond and jointly define an accommodating space having two opposite openings, a positioning space jointly defined at a center of the accommodating space by the two composite surfaces, an inner diameter of the positioning space being greater than an inner diameter of the accommodating space; and
an ultrasonic sensor, placed in the accommodating space, comprising a body portion provided in the positioning space, at least one sensing channel portion provided at the body portion and extending towards opposite directions so as to be located in the accommodating space, at least one piezoelectric unit located at an end surface of the sensing channel portion, and a second channel passing through the body portion; wherein, an outer diameter of the sensing channel portion is slightly smaller than the inner diameter of the accommodating space, such that a gap is formed between the sensing channel portion and the accommodating space, the piezoelectric unit is exposed from one of the openings of the accommodating space to come into contact with an exterior, and the two first channels and the second channel are located on a same axial line.

2. The ultrasonic sensing device of claim 1, wherein the ultrasonic sensor comprises two of the sensing channel portions located at the body portion and respectively extending towards opposite directions, and two piezoelectric units respectively located at one of the end surfaces of the two sensing channel portions, and the two piezoelectric units are respectively exposed from the two openings of the accommodating space to come into contact with the exterior.

3. The ultrasonic sensing device of claim 1, wherein a cross section of the second channel comprises two arc regions arranged at an interval and a flat plane region located between the two arc regions, and the two flat plane regions are parallel to the two end surfaces of the body portion.

4. The ultrasonic sensing device of claim 1, wherein the support body further comprises a noise resistant layer covering outer surfaces of the two cover portions.

5. The ultrasonic sensing device of claim 1, wherein the two cover portions individually comprise a plurality of screw holes formed outside the two recesses and matching one another, the ultrasonic sensing device further comprises a fastening unit, and the fastening unit fixes the two cover portions through the plurality of screw holes.

6. The ultrasonic sensing device of claim 1, wherein each of the recesses is defined by a concave plane formed downwards from the first surface, each of the composite surfaces is formed by two of an inclined plane, a polygon and a curved plane, and the first channel is formed on the composite surface.

7. The ultrasonic sensing device of claim 6, wherein, a height difference exists at each of the two ends of the composite surface, such that a step structure is formed at a junction between the positioning space and the accommodating space.

8. The ultrasonic sensing device of claim 1, wherein the support body further comprises an extension portion extending from the second surface of one of the cover portions towards away from the cover portion, and one of the first channels extends into the extension portion.

9. The ultrasonic sensing device of claim 8, wherein the support body further comprises a fixing portion provided at one end of the extension portion opposite to the cover portion.

* * * * *